(12) United States Patent
Forsyth et al.

(10) Patent No.: US 8,008,032 B2
(45) Date of Patent: Aug. 30, 2011

(54) TAGGED LIGANDS FOR ENRICHMENT OF RARE ANALYTES FROM A MIXED SAMPLE

(75) Inventors: Allyn Forsyth, San Diego, CA (US); Helen Barnes, San Diego, CA (US)

(73) Assignee: Cellective DX Corporation, Mountain View, CA (US)

( * ) Notice: Subject to any disclaimer, the term of this patent is extended or adjusted under 35 U.S.C. 154(b) by 383 days.

(21) Appl. No.: 12/037,077

(22) Filed: Feb. 25, 2008

(65) Prior Publication Data

US 2009/0215088 A1 Aug. 27, 2009

(51) Int. Cl.
*G01N 33/574* (2006.01)
*G01N 37/00* (2006.01)
*G01N 1/18* (2006.01)
*B01L 3/00* (2006.01)

(52) U.S. Cl. .......... 435/7.23; 435/2; 435/7.2; 435/7.5; 435/286.5; 435/287.2; 435/971; 435/973; 436/501; 436/518; 436/56; 436/64; 436/175; 436/177; 436/10; 436/524; 436/528; 436/532; 422/417; 422/502; 422/504

(58) Field of Classification Search .......... 435/2, 7.2, 435/7.23, 7.5, 40.51, 286.6, 287.1, 971, 973, 435/286.5, 287.2; 436/501, 518, 56, 64, 436/167, 175, 177, 813, 524, 528, 532, 10; 422/101, 417, 502, 504
See application file for complete search history.

(56) References Cited

U.S. PATENT DOCUMENTS

| | | | |
|---|---|---|---|
| 5,635,363 A | 6/1997 | Altman et al. |
| 5,693,539 A | 12/1997 | Miltenyi et al. |
| 5,707,799 A | 1/1998 | Hansmann et al. |
| 5,715,946 A | 2/1998 | Reichenbach |
| 5,837,115 A | 11/1998 | Austin et al. |
| 6,156,270 A | 12/2000 | Buechler et al. |
| 6,190,870 B1 | 2/2001 | Schmitz et al. |
| 6,471,860 B1 | 10/2002 | Miltenyi et al. |
| 6,613,525 B2 | 9/2003 | Nelson et al. |
| 6,645,731 B2 | 11/2003 | Terstappen et al. |

(Continued)

FOREIGN PATENT DOCUMENTS

EP 1597353 B1 11/2010

(Continued)

OTHER PUBLICATIONS

Nagrath et al. (Isolation of rare circulating tumour cells in cancer patients by microchip technology (Nature 450: (20/27): 1235-1238 (Dec. 2007)).*
Aggarwal et al. (A combinatorial approach to the selective capture of circulating malignant epithelial cells by peptide ligands, Biomaterials 26: 6077-6086 (2005)).*
Aggarwal, et al. A combinatorial approach to the selective capture of circulating malignant epithelial cells by peptide ligands. Biomaterials. Oct. 2005;26(30):6077-86.

(Continued)

*Primary Examiner* — Gail R Gabel
(74) *Attorney, Agent, or Firm* — Wilson Sonsini Goodrich & Rosati (57) ABSTRACT

Method of enriching specific cells from cellular samples are disclosed, comprising contacting in solution a cellular sample with affinity-tagged ligands (ATLs) each comprising a first ligand linked to an affinity tag, wherein the ligand selectively binds a cellular marker of the rare cells and the affinity tag can be selectively captured by a capture moiety, wherein the affinity tags do not comprise a magnetic particle; and flowing the sample through a microfluidic device comprising the capture moiety to selectively retain ATL-bound cells. Methods for enriching circulating tumor cells, and devices for enriching specific cells from cellular samples are also disclosed.

9 Claims, 8 Drawing Sheets

U.S. PATENT DOCUMENTS

| | | |
|---|---|---|
| 6,913,697 B2 | 7/2005 | Lopez et al. |
| 7,030,228 B1 | 4/2006 | Schmitz et al. |
| 7,150,812 B2 | 12/2006 | Huang et al. |
| 7,166,423 B1 | 1/2007 | Miltenyi et al. |
| 7,190,818 B2 | 3/2007 | Ellis et al. |
| 7,262,269 B2 | 8/2007 | Lam et al. |
| 7,428,325 B2 | 9/2008 | Douglass et al. |
| 7,783,098 B2 | 8/2010 | Douglass et al. |
| 7,785,810 B2 | 8/2010 | Chen |
| 2003/0159999 A1 | 8/2003 | Oakey et al. |
| 2004/0005582 A1 | 1/2004 | Shipwash |
| 2004/0018611 A1 | 1/2004 | Ward et al. |
| 2004/0048360 A1 | 3/2004 | Wada et al. |
| 2004/0144651 A1 | 7/2004 | Huang et al. |
| 2005/0266433 A1 | 12/2005 | Kapur et al. |
| 2005/0282220 A1 | 12/2005 | Prober et al. |
| 2006/0024756 A1 | 2/2006 | Tibbe et al. |
| 2006/0134599 A1 | 6/2006 | Toner et al. |
| 2006/0151265 A1 | 7/2006 | Honjou et al. |
| 2006/0226433 A1 | 10/2006 | Kawano |
| 2006/0252054 A1 | 11/2006 | Lin et al. |
| 2006/0252087 A1 | 11/2006 | Tang et al. |
| 2006/0266692 A1 | 11/2006 | Foster et al. |
| 2006/0285996 A1 | 12/2006 | Ohman et al. |
| 2007/0020772 A1 | 1/2007 | Cao et al. |
| 2007/0026381 A1 | 2/2007 | Huang et al. |
| 2007/0026414 A1 * | 2/2007 | Fuchs et al. ............ 435/6 |
| 2007/0059680 A1 | 3/2007 | Kapur et al. |
| 2007/0160503 A1 | 7/2007 | Sethu et al. |
| 2007/0212737 A1 | 9/2007 | Clarke et al. |
| 2009/0136982 A1 | 5/2009 | Tang et al. |
| 2010/0059414 A1 | 3/2010 | Sturm et al. |
| 2010/0167337 A1 | 7/2010 | Tsinberg et al. |
| 2010/0248358 A1 | 9/2010 | Yoshioka |

FOREIGN PATENT DOCUMENTS

| | | |
|---|---|---|
| WO | WO 02/12896 * | 2/2002 |
| WO | WO 02/12896 A1 | 2/2002 |
| WO | WO 2006/108087 A2 | 10/2006 |
| WO | WO 2007/126938 A2 | 11/2007 |
| WO | WO 2008/017871 A1 | 2/2008 |

OTHER PUBLICATIONS

Fan, et al. Biotin derivatives of methotrexate and folate. Synthesis and utilization for affinity purification of two membrane-associated folate transporters from L1210 cells. J Biol Chem. Aug. 15, 1991;266(23):14862-5.

He, et al. In vivo quantitation of rare circulating tumor cells by multiphoton intravital flow cytometry. Proc Natl Acad Sci U S A. Jul. 10, 2007;104(28):11760-5.

Kurihar, et al. Imaging brain tumors by targeting peptide radiopharmaceuticals through the blood-brain barrier. Cancer Res. Dec. 15, 1999;59(24):6159-63.

Li, et al. Identification and characterization of a novel peptide ligand of epidermal growth factor receptor for targeted delivery of therapeutics. FASEB J. Dec. 2005;19(14):1978-85.

Nagrath, et al. Isolation of rare circulating tumour cells in cancer patients by microchip technology. Nature. 2007; 450: 1235-1241 (with Supplemental pp. 1-10).

Sandoval, et al. Uptake and trafficking of fluorescent conjugates of folic acid in intact kidney determined using intravital two-photon microscopy. Am J Physiol Cell Physiol. Aug. 2004;287(2):C517-26.

* cited by examiner

(Affinity Tag)

| | |
|---|---|
| 2AR | MMP17 |
| A DISINTEGRIN | MOESIN |
| ACTIVATOR OF THYROID AND RETINOIC | MONOCYTE ARGININE-SERPIN |
| ACID RECEPTOR (ACTR) | MONOCYTE-DERIVED NEUTROPHIL |
| ADAM 11 | CHEMOTACTIC FACTOR |
| ADIPOGENESIS INHIBITORY FACTOR (ADIF) | MONOCYTE-DERIVED PLASMINOGEN |
| ALPHA 6 INTEGRIN SUBUNIT | ACTIVATOR INHIBITOR |
| ALPHA V INTEGRIN SUBUNIT | MTS-1 |
| ALPHA-CATENIN | MUC-1 |
| AMPLIFIED IN BREAST CANCER 1 (AIB1) | MUC18 |
| AMPLIFIED IN BREAST CANCER 3 (AIB3) | MUCIN LIKE CANCER ASSOCIATED ANTIGEN |
| AMPLIFIED IN BREAST CANCER 4 (AIB4) | (MCA) |
| AMYLOID PRECURSOR PROTEIN SECRETASE | MUCIN |
| (APPS) | MUC-1 |
| AP-2 GAMMA | MULTIDRUG RESISTANCE PROTEIN 1 (MDR, |
| APPS | MDR1) |
| ATP-BINDING CASSETTE | MULTIDRUG RESISTANCE RELATED PROTEIN-1 |
| TRANSPORTER (ABCT) PLACENTA-SPECIFIC | (MRP, MRP-1) |
| (ABCP) | N-CADHERIN |
| ATP-BINDING CASSETTE SUBFAMILY C | GM-CSF |
| MEMBER (ABCC1) | GRANULOCYTE CHEMOTACTIC PROTEIN 1 |
| BAG-1 | (GCP1) |
| BASIGIN (BSG) | GRANULOCYTE-MACROPHAGE-COLONY |
| BCEI | STIMULATING FACTOR GROWTH FACTOR |
| B-CELL DIFFERENTIATION FACTOR (BCDF) | RECEPTOR BOUND-7 (GRB-7) |
| B-CELL LEUKEMIA 2 (BCL-2) | GSTp |
| B-CELL STIMULATORY FACTOR-2 (BSF-2) | HAP |
| BCL-1 | HEAT-SHOCK COGNATE PROTEIN 70 (HSC70) |
| BCL-2-ASSOCIATED X PROTEIN (BAX) | HEAT-STABLE AssNTIGEN |
| BCRP | HEPATOCYTE GROWTH FACTOR (HGF) |
| BETA 1 INTEGRIN SUBUNIT | HEPATOCYTE GROWTH FACTOR RECEPTOR |
| BETA 3 INTEGRIN SUBUNIT | (HGFR) |
| DIFFERENTIATION-INHIBITING ACTIVITY | HEPATOCYTE-STIMULATING FACTOR III (HSF |
| (DIA) | III) |
| DNA AMPLIFIED IN MAMMARY CARCINOMA | HER-2 |
| 1 (DAM1) | HER2/NEU |
| DNA TOPOISOMERASE II ALPHA | HERMES ANTIGEN |
| DR-NM23 | HET |
| E-CADHERIN | HHM |
| EMMPRIN | NEU |
| EMS1 | NEUTRAL ENDOPEPTIDASE |
| ENDOTHELIAL CELL | NEUTROPHIL-ACTIVATING PEPTIDE 1 (NAP1) |
| GROWTH FACTOR (ECGR) | NM23-H1 |
| PLATELET-DERIVED (PD-ECGF) | NM23-H2 |
| ENKEPHALINASE | NME1 |
| EPIDERMAL GROWTH FACTOR RECEPTOR | NME2 |
| (EGFR) | NUCLEAR RECEPTOR COACTIVATOR-1 (NCoA-1) |
| BETA 5 INTEGRIN SUBUNIT | NUCLEAR RECEPTOR COACTIVATOR-2 (NCoA-2) |
| BETA-2 INTERFERON | NUCLEAR RECEPTOR COACTIVATOR-3 (NCoA-3) |
| BETA-CATENIN | NUCLEOSIDE DIPHOSPHATE KINASE A (NDPKA) |

Figure 3 Continued

| | |
|---|---|
| BETA-CATENIN | NUCLEOSIDE DIPHOSPHATE KINASE B (NDPKB) |
| BONE SIALOPROTEIN (BSP) | ONCOSTATIN M (OSM) |
| BREAST CANCER ESTROGEN-INDUCIBLE SEQUENCE (BCEI) | ORNITHINE DECARBOXYLASE (ODC) |
| BREAST CANCER RESISTANCE PROTEIN (BCRP) | OSTEOCLAST DIFFERENTIATION FACTOR (ODF) |
| | OSTEOCLAST DIFFERENTIATION FACTOR RECEPTOR (ODFR) |
| BREAST CANCER TYPE 1 (BRCA1) | OSTEONECTIN (OSN, ON) |
| BREAST CANCER TYPE 2 (BRCA2) | OSTEOPONTIN (OPN) |
| BREAST CARCINOMA AMPLIFIED SEQUENCE 2 (BCAS2) | OXYTOCIN RECEPTOR (OXTR) |
| | p27/kip1 |
| CADHERIN EPITHELIAL CADHERIN-11 | p300/CBP COINTEGRATOR ASSOCIATE PROTEIN (p/CIP) |
| CADHERIN-ASSOCIATED PROTEIN | |
| CALCITONIN RECEPTOR (CTR) | p53 |
| CALCIUM PLACENTAL PROTEIN (CAPL) | p9Ka |
| CALCYCLIN | PAI-1 |
| CALLA | PAI-2 |
| CAM5 | PARATHYROID ADENOMATOSIS 1 (PRAD1) |
| CAPL | PARATHYROID HORMONE-LIKE HORMONE (PTHLH) |
| CARCINOEMBRYONIC ANTIGEN (CEA) | |
| CATENIN ALPHA 1 | PARATHYROID HORMONE-RECEPTOR EXPRESSION-1 (ICERE-1) |
| CATHEPSIN B | |
| CATHEPSIN D | KAI1 |
| CATHEPSIN K | KDR |
| CATHEPSIN L2 | KERATIN 8 |
| CATHEPSIN O | KERATIN 18 |
| CATHEPSIN O1 | KERATIN 19 |
| CATHEPSIN V | KISS-1 |
| CD10 | LEUKEMIA INHIBITORY FACTOR (LIF) |
| CD146 | LIF |
| CD147 | LOST IN INFLAMMATORY BREAST CANCER (LIBC) |
| CD24 | |
| GAMMA-CATENIN | LOT ("LOST ON TRANSFORMATION") |
| GAP JUNCTION PROTEIN (26 kDa) | LYMPHOCYTE HOMING RECEPTOR |
| GAP JUNCTION PROTEIN (43 kDa) | MACROPHAGE-COLONY STIMULATING FACTOR |
| GAP JUNCTION PROTEIN ALPHA-1 (GJA1) | MAGE-3 |
| GAP JUNCTION PROTEIN BETA-2 (GJB2) | MAMMAGLOBIN |
| GCP1 | MASPIN |
| GELATINASE A | MC56 |
| GELATINASE B | M-CSF |
| GELATINASE (72 kDa) | MDC |
| GELATINASE (92 kDa) | MDNCF |
| GLIOSTATIN | MDR |
| GLUCOCORTICOID RECEPTOR INTERACTING PROTEIN 1 (GRIP1) | P-CADHERIN |
| | PD-ECGF |
| GLUTATHIONE S-TRANSFERASE p | PDGF-β |
| CD29 | PEANUT-REACTIVE URINARY MUCIN (PUM) |
| CD44 | P-GLYCOPROTEIN (P-GP) |
| CD51 | PGP-1 |
| CD54 | PHGS-2 |
| CD61 | PHS-2 |
| CD66e | PIP |
| CD82 | PLAKOGLOBIN PLASMINOGEN ACTIVATOR INHIBITOR (TYPE 1) |
| CD87 | |

Figure 3 Continued

| | |
|---|---|
| CD9 | PLASMINOGEN ACTIVATOR INHIBITOR (TYPE 2) |
| CEA | PLASMINOGEN ACTIVATOR (TISSUE-TYPE) |
| CELLULAR RETINOL-BINDING PROTEIN 1 | PLASMINOGEN ACTIVATOR (UROKINASE-TYPE) |
| (CRBP1) | PLATELET GLYCOPROTEIN IIIa (GP3A) |
| c-ERBB-2 | PLAU |
| CK7 | PLEOMORPHIC ADENOMA GENE-LIKE 1 |
| CK8 | (PLAGL1) |
| CK18 | POLYMORPHIC EPITHELIAL MUCIN (PEM) |
| CK19 | PRAD1 |
| CK20 | PROGESTERONE RECEPTOR (PgR) |
| CLAUDIN-7 | PROGESTERONE RESISTANCE |
| c-MET | PROSTAGLANDIN ENDOPEROXIDE SYNTHASE-2 |
| COLLAGENASE | PROSTAGLANDIN G/H SYNTHASE-2 |
| FIBROBLAST | PROSTAGLANDIN H SYNTHASE-2 |
| COLLAGENASE | pS2 |
| INTERSTITIAL | PS6K |
| COLLAGENASE-3 | PSORIASIN |
| COMMON ACUTE | PTHLH |
| LYMPHOCYTIC LEUKEMIA | PTHrP |
| ANTIGEN (CALLA) | RAD51 |
| CONNEXIN 26 (Cx26) | NEP |
| CONNEXIN 43 (Cx43) | RAD52 |
| CORTACTIN | RAD54 |
| COX-2 | RAP46 |
| CTLA-8 | RECEPTOR-ASSOCIATED COACTIVATOR 3 |
| CTR | (RAC3) |
| CTSD | REPRESSOR OF ESTROGEN RECEPTOR |
| CYCLIN D1 | ACTIVITY (REA) |
| CYCLOOXYGENASE-2 | S100A4 |
| CYTOKERATIN 18 | S100A6 |
| CYTOKERATIN 19 | S100A7 |
| CYTOKERATIN 8 | S6K |
| CYTOTOXIC T-LYMPHOCYTE-ASSOCIATED | SART-1 |
| SERINE ESTERASE 8 (CTLA-8) | SCAFFOLD ATTACHMENT FACTOR B (SAF-B) |
| HUMORAL | SCATTER FACTOR (SF) SECRETED |
| HYPERCALCEMIA OF MALIGNANCY (HHM) | PHOSPHOPROTEIN-1 (SPP-1) |
| ICERE-1 | SECRETED PROTEIN ACIDIC AND RICH IN |
| INT-1 | CYSTEINE (SPARC) |
| INTERCELLULAR ADHESION MOLECULE-1 | STANNICALCIN |
| (ICAM-1) | STEROID RECEPTOR COACTIVATOR-1 (SRC-1) |
| INTERFERON-GAMMA-INDUCING FACTOR | STEROID RECEPTOR COACTIVATOR-2 (SRC-2) |
| (IGIF) | STEROID RECEPTOR COACTIVATOR-3 (SRC-3) |
| INTERLEUKIN-1 ALPHA (IL-1A) | STEROID RECEPTOR RNA ACTIVATOR (SRA) |
| INTERLEUKIN-1 BETA (IL-1B) | STROMELYSIN-1 |
| INTERLEUKIN-11 (IL-11) | STROMELYSIN-3 |
| INTERLEUKIN-17 (IL-17) | TENASCIN-C (TN-C) |
| INTERLEUKIN-18 (IL-18) | TESTES-SPECIFIC PROTEASE 50 |
| INTERLEUKIN-6 (IL-6) | THROMBOSPONDIN I |
| INTERLEUKIN-8 (IL-8) | THROMBOSPONDIN II |
| INVERSELY CORRELATED WITH ESTROGEN | THYMIDINE PHOSPHORYLASE (TP) |
| EPISIALIN | THYROID HORMONE RECEPTOR ACTIVATOR |
| EPITHELIAL MEMBRANE ANTIGEN (EMA) | MOLECULE 1 (TRAM-1) |
| ER-ALPHA | TIGHT JUNCTION PROTEIN 1 (TJP1) |

Figure 3 Continued

| | |
|---|---|
| ERBB2 | TIMP1 |
| ERBB4 | TIMP2 |
| ER-BETA | TIMP3 RELATED PEPTIDE (PTHrP) |
| ERF-1 | TIMP4 |
| ERYTHROID-POTENTIATING ACTIVITY (EPA) | TISSUE-TYPE PLASMINOGEN ACTIVATOR |
| ESR1 | TN-C |
| ESTROGEN RECEPTOR-ALPHA | TP53 |
| ESTROGEN RECEPTOR-BETA | tPA |
| ETS-1 | TRANSCRIPTIONAL INTERMEDIARY FACTOR 2 |
| EXTRACELLULAR MATRIX | (TIF2) |
| METALLOPROTEINASE INDUCER (EMMPRIN) | TREFOIL FACTOR 1 (TFF1) |
| FIBRONECTIN RECEPTOR BETA | TSG101 |
| POLYPEPTIDE (FNRB) | TSP-1 |
| FIBRONECTIN RECEPTOR BETA SUBUNIT | TSP1 |
| (FNRB) | TSP-2 |
| FLK-1 | TSP2 |
| GA15.3 | TSP50 |
| GA733.2 | TUMOR CELL COLLAGENASE STIMULATING |
| GALECTIN-3 | FACTOR (TCSF) |
| MELANOMA CELL ADHESION MOLECULE | TUMOR-ASSOCIATED EPITHELIAL MUCIN |
| (MCAM) | uPA |
| MEMBRANE METALLOENDOPEPTIDASE | uPAR |
| (MME) | UROKINASE |
| MEMBRANE-ASSOCIATED | UROKINASE-TYPE PLASMINOGEN ACTIVATOR |
| NEUTRAL ENDOPEPTIDASE (NEP) | UROKINASE-TYPE PLASMINOGEN ACTIVATOR |
| CYSTEINE-RICH PROTEIN (MDC) | RECEPTOR (uPAR) |
| METASTASIN (MTS-1) | UVOMORULIN |
| MLN64 | VASCULAR ENDOTHELIAL GROWTH FACTOR |
| MMP1 | VASCULAR ENDOTHELIAL GROWTH FACTOR |
| MMP2 | RECEPTOR-2 (VEGFR2) |
| MMP3 | VASCULAR ENDOTHELIAL GROWTH FACTOR-A |
| MMP7 | VASCULAR PERMEABILITY FACTOR |
| MMP9 | VEGFR2 |
| MMP11 | VERY LATE T-CELL ANTIGEN BETA (VLA-BETA) |
| MMP13 | VIMENTIN |
| MMP14 | VITRONECTIN RECEPTOR ALPHA POLYPEPTIDE |
| MMP15 | (VNRA) |
| MMP16 | VITRONECTIN RECEPTOR |
| | VON WILLEBRAND FACTOR |
| | VPF |
| | VWF |
| | WNT-1 |
| | ZAC |
| | ZO-1 |
| | ZONULA OCCLUDENS-1 |

```
                    SEQUENCE LISTING

<160> NUMBER OF SEQ ID NOS: 2

<210> SEQ ID NO 1
<211> LENGTH: 12
<212> TYPE: PRT
<213> ORGANISM: Artificial sequence
<220> FEATURE:
<223> OTHER INFORMATION: Epidermal Growth factor (EGF) peptide

<400> SEQUENCE: 1

Tyr His Trp Tyr Gly Tyr Thr Pro Gln Asn Val Ile
1               5                   10

<210> SEQ ID NO 2
<211> LENGTH: 12
<212> TYPE: PRT
<213> ORGANISM: Artificial sequence
<220> FEATURE:
<223> OTHER INFORMATION: ligand epi peptide

<400> SEQUENCE: 2

Gln Met Ala Arg Ile Pro Lys Arg Leu Ala Arg His
1               5                   10
```

US 8,008,032 B2

TAGGED LIGANDS FOR ENRICHMENT OF RARE ANALYTES FROM A MIXED SAMPLE

BACKGROUND OF THE INVENTION

Analysis of a complex mixture such as blood can be difficult but provides valuable information. For example, CD4 T cell levels can reflect the course of disease in AIDS patients, cellular lymphoid and myeloid markers can aid leukemia and lymphoma diagnoses, and the presence of errant epithelial cells in the blood may signify a metastasizing cancer.

SEQUENCE LISTING

The instant application contains a Sequence Listing which has been submitted in ASCII format via EFS-Web and is hereby incorporated by reference in its entirety. Said ASCII copy, created on Feb. 23, 2011, is named 32055-737.201.txt and is 1 Kilobytes in size.

Such complex mixtures can be analyzed by fluorescent activated cell sorting (FACS), a technology that can quantitate marked analytes and also separate them out from the mixtures. Another popular method of cell separation involves magnetically labeling a target population of cells, e.g. with ferromagnetic beads, followed by sorting the labeled cells by passing them through a receptacle positioned within a magnetic field, a process also known as magnetic activated cell sorting (MACS). Despite their widespread use, FACS and MACS technologies have disadvantages, for example, they require machinery that is expensive and difficult to maintain. FACS technology has the added disadvantage of having limited portability.

Given the heavy demand, new approaches and technologies for cell sorting are needed for medical diagnostics and other applications.

SUMMARY OF THE INVENTION

In one aspect, methods for enriching specific cells in a cellular sample are provided. The methods comprise a method for enriching rare cells from a cellular sample comprising contacting in solution a cellular sample with affinity tagged ligands (ATLs) each comprising a first ligand linked to an affinity tag, wherein the ligand selectively binds a cellular marker of the rare cells and the affinity tag can be selectively captured by a capture moiety, wherein the affinity tags do not comprise a magnetic particle; and flowing the sample through a microfluidic device comprising the capture moiety to selectively retain ATL-bound cells.

In some embodiments, the method comprises a method for enriching rare cells from a cellular sample comprising: contacting in solution the cellular sample with affinity-tagged ligands (ATLs) each comprising: a ligand linked to a plurality of affinity tags, wherein the ligand selectively binds a cellular marker of the rare cells and the affinity tag can be selectively captured by a capture moiety and wherein the ratio of ligand: affinity tag of the ATL's is less than 1:1; flowing the sample through a microfluidic device comprising the capture moiety to selectively retain ATL-bound cells.

In one aspect, methods for enriching specific cells in a cellular sample are provided. The methods comprise a method for enriching rare cells, wherein the rare cells are circulating tumor cells or epithelial cells, from a cellular sample comprising contacting in solution a cellular sample with affinity-tagged ligands (ATLs) each comprising a first ligand linked to an affinity tag, wherein the ligand is folic acid, Dolichos Biflorus Agglutinin (DBA), epidermal growth factor (EGF), EGF peptide (amino acid sequence YHWYGYTPQNVI (SEQ ID NO:1), epi peptide (amino acid sequence QMARIPKRLARH (SEQ ID NO:2), transforming growth factor-alpha (TGF-alpha), Urokinase Plasminogen Activator (UPA), FasL, MUC1/sec, catenin, ICAM-1, plasminogen, or the like and selectively binds a cellular marker of the rare cells and the affinity tag can be selectively captured by a capture moiety, wherein the affinity tags comprise biotin, desthiobiotin, histidine, polyhistidine, myc, hemagglutinin (HA), FLAG, fluorescence tag, tandem affinity purification (TAP) tags, FLAG, or glutathione S transferase (GST) or derivatives thereof; and flowing the sample through a microfluidic device comprising the capture moiety to selectively retain ATL-bound cells; wherein the capture moiety comprises avidin, streptavidin, Neutravidin™, nickel, or glutathione or other molecule capable of binding the affinity tag; and wherein the cellular marker is a cancer marker for one or more of breast, prostate, liver, ovary, skin, colon, rectum, cervix, esophagus, stomach, brain, lung, or endometrium cancer.

In some embodiments, the method comprises a method for enriching rare cells from a cellular sample comprising: contacting in solution the cellular sample with affinity-tagged ligands (ATLs) each comprising: a ligand linked to a plurality of affinity tags, wherein the ligand is folic acid or epidermal growth factor (EGF) and selectively binds a cellular marker of the rare cells wherein the rare cells are circulating tumor cells or epithelial cells, and the affinity tag and wherein the ratio of ligand:affinity tag of the ATL's is less than 1:1; flowing the sample through a microfluidic device comprising the capture moiety to selectively retain ATL-bound cells.

In one aspect, methods for enriching specific cells in a cellular sample are provided. The methods comprise a method for enriching rare cells, wherein the rare cells are circulating tumor cells or epithelial cells, from a cellular sample comprising contacting in solution a cellular sample with affinity-tagged ligands (ATLs) each comprising a first ligand linked to an affinity tag, wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR) and selectively binds a cellular marker of the rare cells and the affinity tag can be selectively captured by a capture moiety, wherein the affinity tags comprise biotin, desthiobiotin, histidine, polyhistidine, myc, hemagglutinin (HA), FLAG, fluorescence tag, tandem affinity purification (TAP) tags, FLAG, or glutathione S transferase (GST) or derivatives thereof, and flowing the sample through a microfluidic device comprising the capture moiety to selectively retain ATL-bound cells; wherein the capture moiety comprises avidin, streptavidin, Neutravidin™, nickel, or glutathione or other molecule capable of binding the affinity tag; and wherein the cellular marker is a cancer marker for one or more of breast, prostate, liver, ovary, skin, colon, rectum, cervix, esophagus, stomach, brain, lung, or endometrium cancer.

In some embodiments, the method comprises a method for enriching rare cells from a cellular sample comprising: contacting in solution the cellular sample with affinity-tagged ligands (ATLs) each comprising: a ligand linked to a plurality of affinity tags, wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR) and selectively binds a cellular marker of the rare cells wherein the rare cells are circulating tumor cells or epithelial cells, and the affinity tag and wherein the ratio of ligand:affinity tag of the ATL's is less than 1:1; flowing the sample through a microfluidic device comprising the capture moiety to selectively retain ATL-bound cells.

In some embodiments, the method comprises a method for enriching rare analytes from a sample comprising: contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; and contacting the sample with the capture moiety to selectively enrich the rare analytes.

In some embodiments, the method comprises a method for enriching rare analytes from a sample comprising:contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; contacting the sample with the capture moiety to selectively enrich the rare analytes; wherein the first affinity tag and said second affinity tag are identical; and wherein the ligand is folic acid, (DBA), EGF; EGF peptide (amino acid sequence YHWYGYTPQNVI (SEQ ID NO:1), epi peptide (amino acid sequence QMARIPKRLARH (SEQ ID NO:2), TGF-alpha; Urokinase Plasminogen Activator (UPA), FasL, MUC1/sec, catenin, ICAM-1, plasminogen, or the like, or wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR).

In some embodiments, the method comprises a method for enriching rare analytes such as cells from a sample such as a blood sample comprising: contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; contacting the sample with the capture moiety to selectively enrich the rare analytes; wherein the mixture of ATL's comprises at least 3, 4, 5, 6, 7, 8, 9, or 10 ATL's each of which comprises an affinity tag that can be selectively captured by the first capture moiety;

In some embodiments, the method comprises a method for enriching rare analytes such as cells from a sample such as a blood sample comprising: contacting in solution said sample with a plurality of affinity-tagged ligands (ATLs) wherein said mixture of ATL's comprises: a first ATL comprising a first ligand that selectively binds a first marker of rare analytes, wherein the first ligand is linked to a first affinity tag that is selectively captured by a first capture moiety; and a second ATL comprising a second ligand that selectively binds a second marker of rare analytes, wherein said second ligand is linked to a second affinity tag, wherein the second affinity tag is selectively captured by the first capture moiety; contacting the sample with the capture moiety to selectively enrich the rare analytes; wherein the mixture of ATL's comprises at least 1, 2, 3, 4, 5, 6, 7, 8, 9, or 10 ATL's each of which comprises an affinity tag that can be selectively captured by the first capture moiety; and wherein each of the ATL's comprises a ratio of Ligand:Affinity Tag that is less than 1:5; and wherein the capture moiety is in a microfluidic device such as a microfluidic device comprising an array of obstacles; wherein the first or second ligand is folic acid, (DBA), EGF; EGF peptide (amino acid sequence YHWYGYTPQNVI (SEQ ID NO:1), epi peptide (amino acid sequence QMARIPKRLARH (SEQ ID NO:2), TGF-alpha; Urokinase Plasminogen Activator (UPA), FasL, MUC1/sec, catenin, ICAM-1, plasminogen, or the like, or wherein the ligand is an antibody that is anti-EpCam; anti-E-Cadherin, anti-Mucin-1, anti-Cytokeratin (CK) 8, anti-epidermal growth factor receptor (EGFR), anti-cytokeratin (CK)19, anti-ErbB2, anti-PDGF, anti-L6, or anti-leukocyte associated receptor (LAR); and wherein the affinity tag comprises biotin, desthiobiotin, histidine, polyhistidine, myc, hemagglutinin (HA), FLAG, fluorescence tag, tandem affinity purification (TAP) tags, FLAG, or glutathione S transferase (GST) or derivatives thereof; wherein the ligand is linked to the affinity tag either directly or via a linker comprising modified dextran, polyethylene glycol, polypropylene glycol, polyvinyl alcohol, or polyvinylpyrrolidone; and wherein the capture moiety comprises avidin, streptavidin, Neutravidin ™, nickel, or glutathione or other molecule capable of binding the affinity tag.

In some embodiments, the method comprises a method of diagnosing a condition such as cancer in a patient comprising: enriching rare cells from the patient through any of the methods described herein; and evaluating, identifying, or quantitating the ATL bound cells.

In some embodiments, the invention comprises a reagent comprising a plurality of affinity tagged ligands each of which comprises a ligand that selectively binds a different cancer cellular marker linked to an identical affinity tag that is selectively captured by a capture moiety wherein the ratio of ligand:affinity tag per ATL is less than 1:1; wherein the reagent comprises at least 1, 2, 3, 4, or 5 different ATL's.

In some embodiments, the device comprises a microfluidic device comprising an array of obstacles, wherein the obstacles are functionalized with capture moieties comprising EGF-peptide, EPI-peptide, folate or DBA.

INCORPORATION BY REFERENCE

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

The present disclosure provides compositions, methods and devices for the detection and isolation of rare analytes from a mixed sample. Rare analytes include cells and particles, such as eukaryotic cells, prokaryotic cells, cellular organelles, cellular fragments, viruses, nucleic acids, proteins, and protein complexes. A mixed sample may include a fluid sample, e.g., water, air, bodily fluids such as blood, urine, etc. A mixed sample may also include a solid sample that is liquefied, e.g., a tumor biopsy, food solids, etc.

Enrichment, detection, and isolation of rare analytes is accomplished using affinity-tagged ligands (ATLs). An ATL may comprise Formula I:

$$L_x\text{-}AT_n,\quad\text{(Formula I)}$$

wherein:

L is a ligand that selectively binds a marker for a rare analyte;

x is the number of ligands within each ATL;

AT is an affinity tag which can be selectively captured using a capture moiety; and n is the number of ATs linked to the ligand.

L and AT may be linked together directly or indirectly (via a linker). Linkers may be straight or branched. A linker may be a peptide, polypeptide, protein, and the like. In some embodiments, the linker moiety is a branched polymer. Such branched polymers include modified dextran, polyethylene glycol, polypropylene glycol, polyvinyl alcohol, polyvinylpyrrolidone, polyethylene acrylamide and combinations thereof. In some embodiments, the linker is branched and comprises multiple ATs. For example, in some embodiments an ATL comprises at least 5, 10, 15, 20, 25, 30, 35, 40, 50, 60, 70, 80, 90,100 or more ATs per L. When a single ligand is linked to multiple AT's, the AT's can each be linked to the ligand via a single linker or via a plurality of linkers (e.g., one linker per AT).

Examples of ligands contemplated in the methods herein include ligands that selectively bind cell surface marker(s) (e.g., receptors and adhesion molecules) of rare cells of interest. A ligand can comprise molecule(s), peptide(s), polypeptides, particles, and the like, and/or fragments thereof. The ligand can be naturally occurring or artificially synthesized. Rare cells include circulating tumor cells (CTCs), circulating epithelial cells or circulating stem cells.

Figure 3:
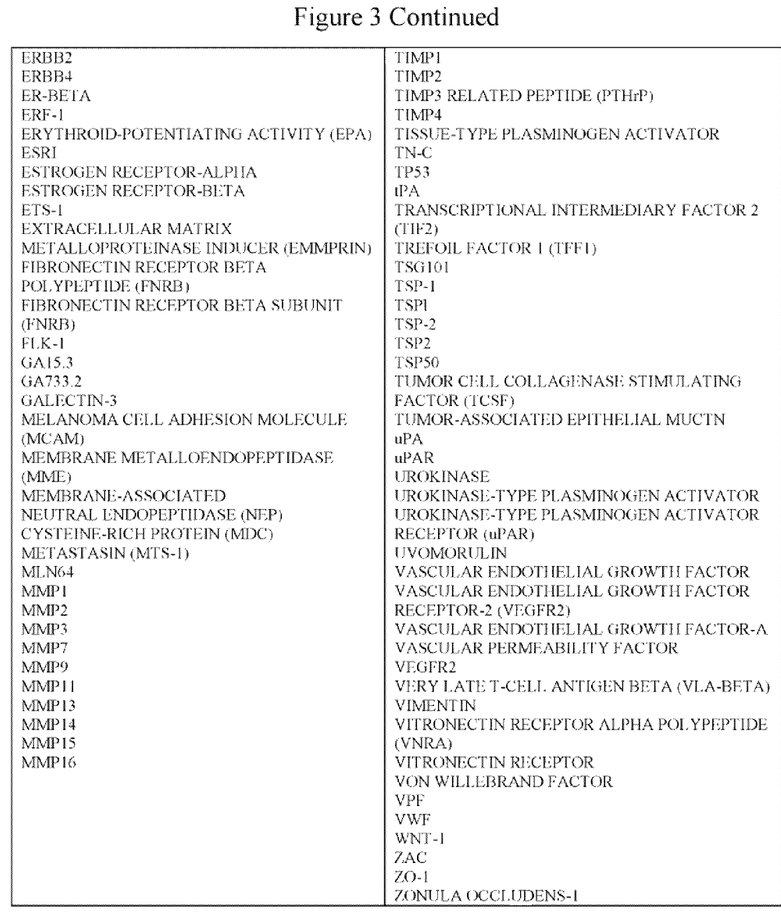
FIG. 3 is a Table of exemplary markers contemplated herein.

In some embodiments, a ligand comprises an antibody, such as a monoclonal antibody or a polyclonal antibody. Examples of ligand antibodies contemplated herein include antibodies that selectively bind CTCs, circulating epithelial cells, or circulating stem cells. In some embodiments, such antibodies selectively bind an antigen such as EpCam; E-Cadherin, Mucin-1, Cytokeratin (CK) 8, epidermal growth factor receptor (EGFR), cytokeratin (CK) 19, ErbB2, PDGF, L6, or leukocyte associated receptor (LAR). In certain embodiments, the ligand may be an antibody to a marker listed in FIG. 3.

In other embodiments, a ligand is not an antibody. Examples of non-antibody ligands include folic acid, Dolichos Biflorus Agglutinin (DBA), epidermal growth factor (EGF), EGF peptide (amino acid sequence YHWYGYT-PQNVI (SEQ ID NO:1), epi peptide (amino acid sequence QMARIPKRLARH (SEQ ID NO:2), transforming growth factor-alpha (TGF-alpha), Urokinase Plasminogen Activator (UPA), FasL, MUC1/sec, catenin, ICAM-1, plasminogen, or the like. In some embodiments, the ligand activates a cellular process, and in other embodiments, the ligand may not activate a cellular process.

An ATL may have a single ligand or multiple ligands (e.g., x>1, or x>2, 5, 10, 20, or more). When an ATL comprises multiple ligands, each ligand may be identical to the other ligands, different from the other ligands, or a combination thereof.

Affinity tags (AT) can include molecules, peptides, polypeptides, particles, and/or other substances capable of being captured by a capture moiety or enrichment device. Examples of ATs include biotin, desthiobiotin, histidine, poly-histidine, glutathione S transferase (GST), myc, hemagglutinin (HA), FLAG, fluorescent tag, tandem affinity purification (TAP) tags, or derivatives thereof. The TAP tag may comprise calmodulin-binding protein, TEV, and protein A or G subunit. In some embodiments, the affinity tag comprises a magnetic particle. In other embodiments, the affinity tag is a molecule or particle other than a magnetic particle. In some instances, an affinity tag does not comprise an antibody.

As described above, an ATL may comprise one AT, or, for example, may comprise at least 2, 5, 10, 20, 30, 40, 50, 60, 70, 80, 90, 100, or more ATs.

To detect rare analytes (or single analyte) in a fluid sample, the sample is mixed with a homogenous or heterogeneous set of ATLs. The sample is incubated with the ATLs for a sufficient amount of time to enable binding of the ligands to the receptors or rare analytes. The sample and ATLs are then applied to one or more capture moieties that selectively bind the affinity tags, thereby allowing enrichment of the bound rare analytes. The capture moiety can be coupled to a solid support (e.g. a tube, a flat substrate, or an array of obstacles).

To detect rare analytes in a solid or semi-solid sample, the sample is first solubilized and then mixed with the mixture of ATLs as described above. Once the sample is incubated with the ATLs for a sufficient period of time to allow binding between the ligands and the rare analyte markers, the sample is applied to one or more capture moieties that selectively binds to the affinity tag.

Capture moieties may be inorganic molecules, organic molecules, peptides, polypeptides, and/or antibodies, and the like, or may include fragments of, or derivatives, of same. The capture moieties are capable of binding to, or interacting with, an affinity tag. Examples of capture moieties include, but are not limited to, a magnet or magnetized substrate, avidin, streptavidin, Neutravidin™, glutathione, nickel, calcium/calmodulin, or IgG. Other examples of capture moieties include magnetic or magnetized surfaces, avidin and avidin-coated particles.

In some instances, capture moieties are part of a microfluidic device (e.g., a microfluidic gap or channel coated with capture moieties). A microfluidic device contemplated herein can comprise an array of obstacles that form a network of microfluidic channels.

The affinity tags can bind irreversibly or reversibly to the capture moiety(ies). In some instances, an affinity tag may be releasable from the capture moiety. For example, desthiobiotin may be used as an affinity tag with avidin as the capture moiety. The bond between biotin and avidin can then be released by applying desphio-biotin or biotin to the sample.

In one example, the ATL's herein can be used to enrich rare analytes such as cells from a mixed sample such as blood. Such method comprises the step of contacting in solution a test sample with affinity-tagged ligands (ATLs). Each ATL comprises: at least one ligand linked to at least one affinity tag. The ligand and affinity tag are optionally liked via a linker comprising one or more of modified dextran, polyethylene glycol, polypropylene glycol, polyvinyl alcohol, or polyvinylpyrrolidone.

The ligands of the ATL's selectively bind a one or more markers of the rare analytes. The affinity tags of the ATLs are ones that can be selectively captured by a single capture moiety or a plurality of capture moieties. Examples of capture moieties contemplated for any of the embodiments herein include avidin, streptavidin, Neutravidin™, nickel, or glutathione. The affinity tags may be one that does not comprise a magnetic particle. Examples of affinity tags include biotin, desthiobiotin, histidine, polyhistidine, myc, hemagglutinin (HA), FLAG, fluorescence tag, tandem affinity purification (TAP) tags, FLAG, glutathione S transferase (GST) or derivatives thereof. After incubation for a sufficient amount of time to allow the sample and ATL's to mix, the mixed sample is contacted with one or more capture moieties or is flowed through a microfluidic device comprising the one or more capture moieties. This selectively retains ATL-bound analytes or cells.

In some instances, each ATL comprises a ratio of ligand to affinity tag such that there are more affinity tags for each ligand. In some instances the ligand:affinity tag ratio is less than 1:1 or less than 1:5 or less than 1:10 or less than 1:100. Furthermore, a single ATL can have at least 2, 3, 4, 5, 6, 7, 8, 9 or 10 different ligands. Each of the ligands can be specific to a different marker, such as a cancer marker.

Cellular cancer markers contemplated herein include markers for a cancer such as breast, prostate, liver, ovary, skin, colon, rectum, cervix, esophagus, stomach, brain, lung, pancreatic, or endometrium cancer. In some instances a cellular marker is epidermal growth factor receptor (EGFR), EPCAM, or folic acid receptor. In some instances, the cellular marker is E-Cadherin, Mucin-1, Cytokeratin (CK) 8, cytokeratin (CK)19, ErbB2, PDGF, L6, or leukocyte associated receptor (LAR) In other instances it is any marker listed in the table of FIG. 3.

To enrich rare analytes such as rare cells (epithelial cells or CTC) found in bodily fluid (e.g., blood), the ligands in the ATL's can be one or more of the following: folic acid, epidermal growth factor (EGF), transforming growth factor-alpha (TGF-alpha), Urokinase Plasminogen Activator (UPA), FasL, MUC1/sec, catenin, ICAM-1, plasminogen, or fragments thereof. In some embodiments, the ligands comprise haptens. In some instances, the ligand is an antibody and in others it is not an antibody.

In some instances, a reagent used to enrich/detect rare analytes comprises a plurality of affinity-tagged ligands (ATLs) wherein each ATL comprises: a first ATL comprising a first ligand that selectively binds a first marker of the rare analytes linked to a first affinity tag that is selectively captured by a first capture moiety; and a second ATL comprising a second ligand that selectively binds a second marker linked to a second affinity tag, wherein the second affinity tag is selectively captured by the first capture moiety. In such embodiments, the reagent described above is mixed with a mixed sample of analytes. After allowing the ATL's and sample to mix for a sufficient amount of time for binding to occur, the sample/ATL mixture is contacted with the first capture moiety to selectively enrich the rare analytes. The capture moiety can be avidin and the capture moiety can be in a muicrofluidic gap or channel. The first and second affinity tags can be identical (both biotin) or different (biotin and desphio-biotin) but both selectively captured by the same capture moiety. In some instances, a mixed sample such as the one described above is contacted with at least 3, 4, 5, 6, 7, 8, 9, or 10 different ATL's each of which comprises an affinity tag that can be selectively captured by a single capture moiety or the same affinity tag.

A sample, such as a blood sample, can be mixed with one or more different ATLs. In certain embodiments, ATLs of similar configuration may be contacted with the targeted analytes. In other embodiments, a mixture of different ATLs may be used. In still other embodiments, step-wise purification of the analyte may occur through sequential use of the same or different ATLs.

An exemplary ATL can have a single ligand comprising anti-EpCAM antibody linked to a plurality of ATs, each of which comprises a biotin molecule. The ATs are linked to the ligand via a branched linker such that each ligand is coupled to at least five ATs. In some embodiments, the ligand may bind the marker (EpCAM) at more than one site. In other embodiments, e.g., EGF, the ligand binds the marker only once. Once the sample is mixed with the ATLs, the sample flows through a microfluidic device, optionally comprising an array of obstacles, coated with avidin capture moieties. Enriched rare cells (e.g., circulating epithelial cells) can then be visualized/detected using any means known in the art, including fluorescent in situ hybridization (FISH) staining.

Some applications may require analysis downstream of the capture of the ATL-bound cells. In some embodiments, the ATLs may be conjugated to one or more detectable labels. Such detectable labels comprise fluorescent markers, HRP-alkaline phosphatase detection or quantum dots. In some embodiments, in addition to an ATL, the cells may be contacted with a detectably-labeled ligand specific for a cellular marker. Such detectable labels may comprise one or more of fluorescent probes, magnetic particles, or quantum dots. The detectably-labeled ligands comprise the ligands described herein relating to ATLs. An example of a detectably-labeled ligand is a fluorescently-labeled antibody.

Varying the number of affinity tags and/or ligands in a single ATL may affect the ability to capture target analytes. Thus, the disclosure provides ATLs with more than one affinity tag and/or more than one ligand. The affinity tags may be identical tags, similar tags, or different tags. Since higher affinity-tag-to-ligand ratios may result in enhanced or more efficient capture of cells, the ratio of affinity tag to ligand in a single ATL may be greater than or equal to 1, for example, 2:1, 3:1, 4:1, 5:1, 10:1, 20:1, or greater.

In some embodiments, the marker is a marker for one or more of the following: cancer of the breast, lung, prostate, liver, ovary, skin, colon, rectum, cervix, esophagus, stomach, brain, bladder, kidney, testicular, or endometrium. In some embodiments, the marker is for a blood cancer such as leukemia or lymphoma.

In some embodiments, vascular disease is monitored by enriching for cells with endothelial markers. Other cancers may also be monitored by enriching for endothelial cells. In some embodiments, fetal markers (e.g. Y chromosome proteins, gamma globin) are used for capturing fetal cells in the maternal circulation. In some embodiments, stem cell markers (CD44) are used to capture stem cells.

In certain embodiments, the methods provided comprise contacting a cellular sample with one or more ATLs to enable binding to one or more cellular markers, followed by capture of the bound cells by an enrichment device. The contacting of the cellular sample with one or more ATLs may occur under conditions pre-determined to maximize binding efficiency. In some embodiments, the conditions may be optimized to minimize non-specific binding. For example, the timing of the contacting between the cellular sample and the one or more ATLs may be optimized. Such optimized or predetermined amount of time may be used for the contacting step. Likewise, conditions for the temperature of the contacting step may be optimized to maximize binding efficiency and/or to minimize internalization of cellular markers. A pre-determined or optimized temperature or temperatures may be used for the contacting step. In some embodiments, the composition of the solution containing the cellular sample and/or the ATL may be optimized for more efficient binding. Blocking reagents or serums may be added to aid in binding efficiency. Examples of such blocking reagents include bovine serum albumin (BSA), fetal calf serum (FCS), milk, and other commercially-obtainable reagents.

The methods may further comprise a wash step in which unbound (or free) ATL is removed from the cellular sample prior to capture by the enrichment device. For example, the wash step could be accomplished by one or more rounds comprising centrifugation of the cellular sample, aspiration of the supernatant, and re-suspension of the cellular sample in wash buffer. The composition of the wash buffer may comprise buffered solutions and may be optimized to maximize binding efficiency. The optimized wash buffer may comprise one or more blocking reagents or serums described herein.

In some embodiments, the cells are added to an enrichment device that comprises a surface functionalized with a capture moiety recognizing the affinity tag or a cellular marker, such as a receptor. In certain embodiments, a surface of the enrichment device is coated or treated with one or more capture moieties (e.g., avidin or Neutravidin) in order to allow capture of the ATL-bound cells. In certain embodiments, such capture-moieties are not antibodies. In some embodiments, such capture moieties are ligands. In some embodiments, the enrichment device comprises a surface coated or functionalized with a ligand that is used to directly enrich cells expressing a specific marker from a mixed cell population. In some embodiments, the surface of such enrichment device is functionalized with folate in order to enrich cells expressing the folate receptor. In some embodiments, the enrichment device is functionalized with Dolichos Biflorus Agglutinin (DBA), epidermal growth factor (EGF), EGF peptide (amino acid sequence YHWYGYTPQNVI (SEQ ID NO:1), epi peptide (amino acid sequence QMARIPKRLARH (SEQ ID NO:2), transforming growth factor-alpha (TGF-alpha), Urokinase Plasminogen Activator (UPA), FasL, MUC1/sec, catenin, ICAM-1, plasminogen, or the like. Parameters such as timing, temperature, and/or buffer composition may be optimized to promote optimal capture by the enrichment device.

The enrichment device may include one or more arrays of obstacles that allow lateral displacement of cells and other components of fluids. Such arrays of obstacles comprise different configurations. In one configuration, a row or rows of obstacles are arranged with a 50% offset from other randomly- or non-randomly-arranged obstacles creating restricted and expanded gaps.

In some embodiments, the obstacles within the array of obstacles are coated or treated with one or more capture moieties or ligands. In some embodiments, the enrichment device is capable of sorting cells based on another variable, e.g. hydrodynamic size, as well as capturing ATL-bound cells. Enrichment devices include, but are not limited to centrifuge, microfuge and ultracentrifuge test tubes. In some embodiments, the enrichment device is a column or other such receptacle such as a magnetic activated cell sorting (MACS) column.

Any of the ATLs herein may be designed to enrich cancer cells as well as prognose and diagnose cancer conditions. For example, cancer can be staged or diagnosed by enriching rare cells (e.g., epithelial cells, circulating cancer stem cells) using ATL's by any of the means described above. Subsequently, the enriched cells can be further evaluated or quantified. In one instance, diagnosis or prognoses comprises comparing the percentage or quantity of epithelial cells in the blood of a test subject with that in the blood of a healthy control subject, a panel of healthy control subjects, known standard levels, or similar information obtained from the same patient at a different point in time.

Peptide Library

In some embodiments, the present disclosure provides a method for screening a combinatorial peptide library for peptide ligands capable of binding cell surface markers. Such methods comprise contacting a sample of cancer cells with a combinatorial peptide library, wherein the peptides have been pre-labeled with one or more affinity tags, described herein; purifying out the cells selectively binding to candidate peptide ligands; and identifying the candidate ligands bound to the cells. In certain embodiments, the purifying may comprise the lateral flow of the cellular sample through a device coated with capture moieties that selectively bind the ATs so as to permit capture of the ATL bound cells

EXAMPLES

Example 1

Capture of H1650 Lung Cancer Cells with Biotinylated Anti-EpCam Antibody

Figure 1A:
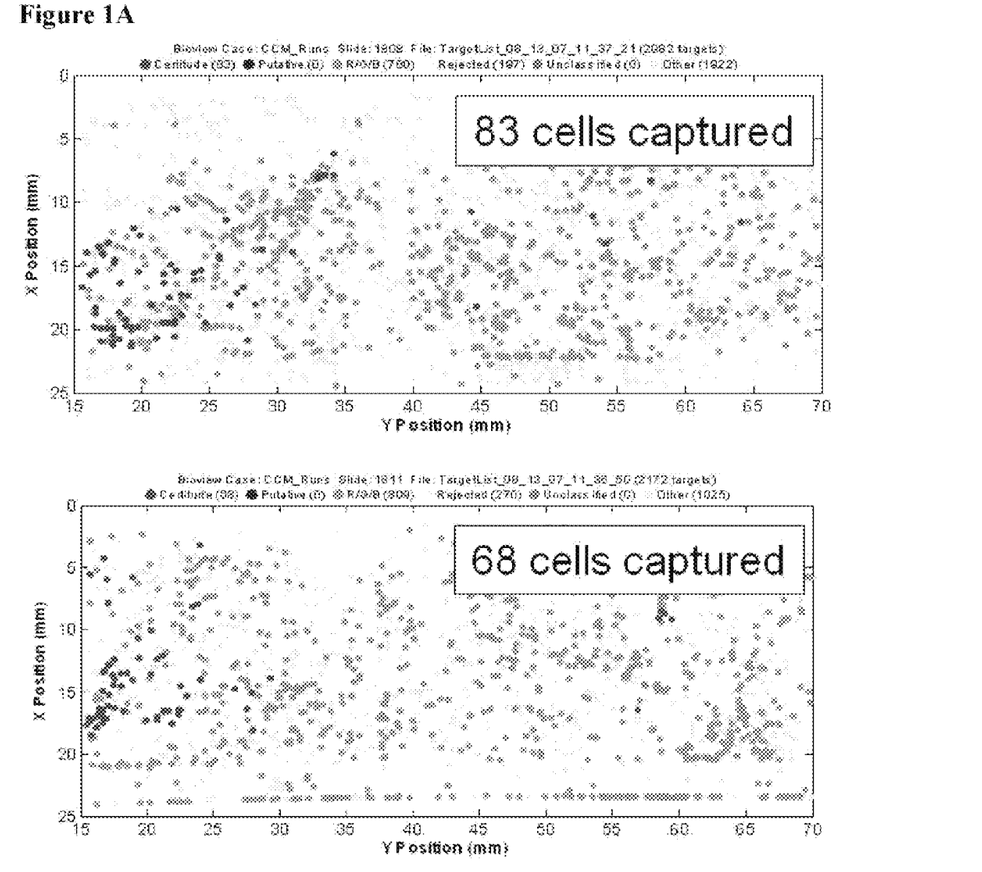
FIG. 1A is a fluorescent image illustrating the capture of lung cancer cells with a non-specific affinity tagged ligand (biotinylated anti-IgG).
Figure 1B:
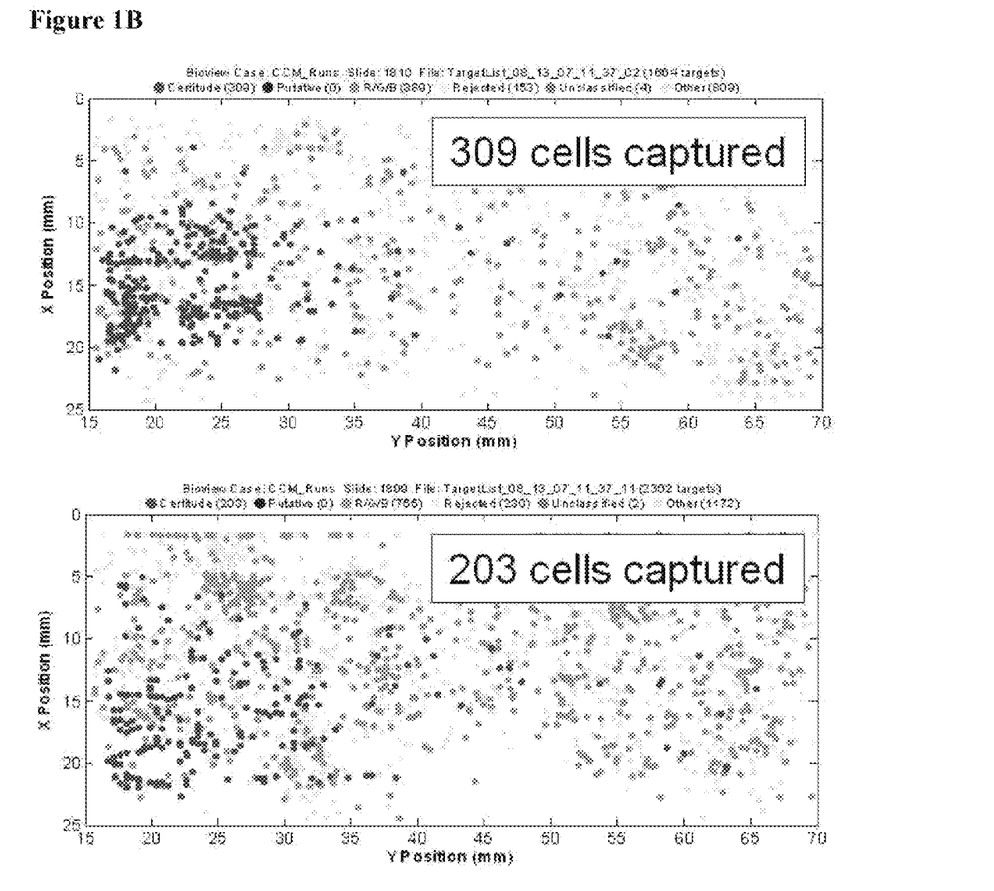
FIG. 1B is a fluorescent image illustrating the capture of lung cancer cells with biotinylated anti-EpCam antibody, an antibody that is specific for an epithelial cell marker present on lung cancer cells.

The example depicted in FIG. 1 illustrates a method and device for isolating cancer cells. The affinity-tagged ligand (ATL) in this example comprised biotin as the affinity tag. The ligand was anti-Epithelial Cell Adhesion Molecule (EpCam) antibody which recognizes an epithelial cellular marker. For the experiment, H1650 lung cancer cells were incubated with biotinylated goat anti-EpCam antibody for 1 hour on ice (FIG. 1B). Approximately 1000 cells were input into each experiment. The left and right images represent replicate experiments. As a negative control, H1650 lung cancer cells were incubated with biotinylated goat IgG antibody under the same or similar conditions (FIG. 1A). Following the incubation, the cells were washed and run through an array of obstacles [comprising a restricted gap—Chip 7, please confirm] chip coated with Neutravidin™. Cells were then fixed and visualized by fluorescence microscopy.

The results of this experiment demonstrated that it is possible to use ATLs to isolate cancer cells. In this example, between 20 and 30% of the total H1650 lung cancer cell population were recovered when anti-EpCam antibody was used as the ligand. To calculate the percentage (%), the # of cells captured was divided by the total # of cells passed onto the chip, and the resulting value was multiplied by 100. In contrast, only 7-8% of cells were recovered when the goat IgG was used.

Example 2

Figure 2:
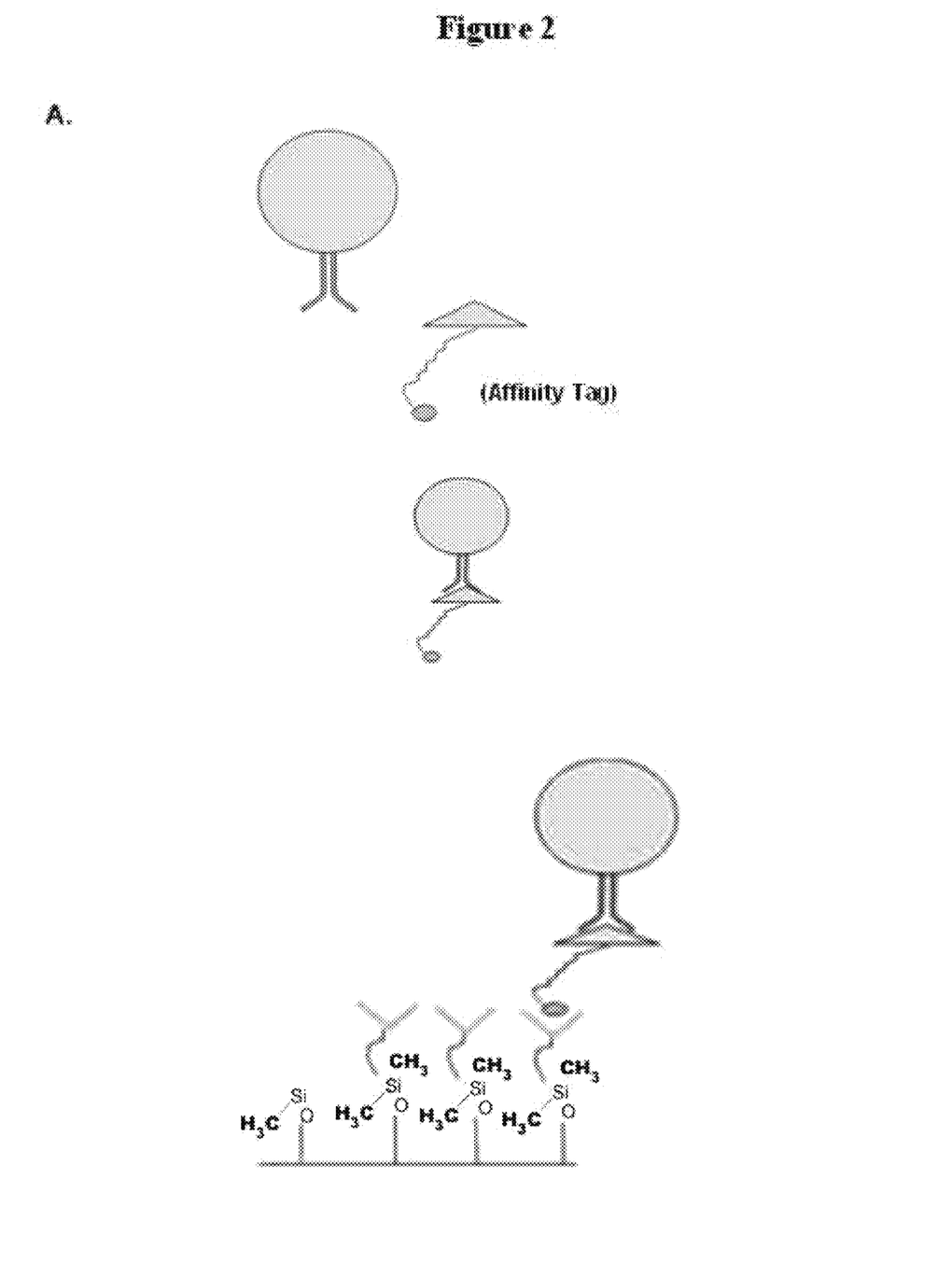
FIG. 2A is a diagram illustrating the capture of cells with a ligand tagged with an affinity tag such as biotin, histidine, or a magnetic particle (top panel), and the affinity-based capture of such cells using a microfluidic chip coated with a capture moiety capable of interacting with the affinity tag (bottom panel).
FIG. 2B is a fluorescent image illustrating the capture of cells bound to Biotin-tagged EGF using a microfluidic device coated with Avidin, a capture moiety capable of interacting with the affinity tag.

Capture of cells after solution phase binding of the cells with an affinity-tagged ligand The examples depicted in FIG. 2 illustrate the capture of cells labeled with an affinity tag before being subjected to a microfluidic device. FIG. 2A is a diagram depicting a cell being contacted with an affinity-tagged ligand in solution (top panel) and the capture of such cell with a microfluidic device coated with a capture moiety capable of recognizing the affinity-tag (lower panel).

FIG. 2B illustrates the capture of cells bound to EGF peptide tagged with biotin. In this example, MDA-MB-231 cells (a breast cell line which expresses low levels of EpCam) were contacted with biotin-tagged EGF peptide in solution under conditions favorable for binding. The cells were then subjected to a chip coated with neutravidin, a capture moiety capable of recognizing the affinity tag. Following fixation, the captured cells were visualized by fluorescent microscopy. The results demonstrate significant capture of cells using this method.

What is claimed is:

1. A method for enriching rare cells from a cellular sample comprising:

(a) contacting in solution said cellular sample with affinity-tagged ligands (ATLs) each ATL comprising:

a first ligand linked to an affinity tag, wherein said ligand selectively binds a cellular marker of said rare cells, said affinity tag can be selectively captured by a capture moiety, and said affinity tag does not comprise a magnetic particle; and (b) flowing said cellular sample containing said ATLs through a microfluidic device comprising a substrate coated with said capture moiety to thereby selectively retain ATL-bound cells by binding said affinity tag to said capture moiety.

2. The method of claim 1, wherein said rare cells are circulating tumor cells or epithelial cells.

3. The method of claim 1, wherein said ligand is folic acid, epidermal growth factor (EGF), Dolichos Biflorus Agglutinin (DBA), EGF peptide, epi peptide, transforming growth factor-alpha (TGF-alpha), Urokinase Plasminogen Activator (UPA), FasL, MUC1/sec, catenin, ICAM-1, or plasminogen.

4. The method of claim 1, wherein said ligand is an antibody.

5. The method of claim 4, wherein said antibody is anti-EpCam, anti-ErbB2, or anti-CK19 antibody.

6. The method of claim 1, wherein said ligand is not an antibody.

7. The method of claim 1, wherein said affinity tag is biotin, desthiobiotin, histidine, polyhistidine, myc, hemagglutinin (HA), FLAG, fluorescence tag, tandem affinity purification (TAP) tags, or glutathione S transferase (GST) or derivatives thereof.

8. The method of claim 1, wherein said ATLs comprises: (a) a first ATL comprising a first ligand that selectively binds a first cellular marker of the rare cells., wherein said first ligand is linked to a first affinity tag, and (b) a second ATL comprising a second ligand that selectively binds a second cellular marker of the rare cells, wherein said second ligand is linked to a second affinity tag, wherein the first ligand and the second ligand are different.

9. The method of claim 1, wherein said ATLs comprises at least 3, 4, 5, 6, 7, or 8 different ATLs, each comprising a ligands, which selectively binds a different cellular marker of the rare cells.

* * * * *

UNITED STATES PATENT AND TRADEMARK OFFICE
CERTIFICATE OF CORRECTION

| | | |
|---|---|---|
| PATENT NO. | : 8,008,032 B2 | Page 1 of 1 |
| APPLICATION NO. | : 12/037077 | |
| DATED | : August 30, 2011 | |
| INVENTOR(S) | : Forsyth et al. | |

It is certified that error appears in the above-identified patent and that said Letters Patent is hereby corrected as shown below:

In Column 12, Line 27, Claim 8; "comprises" should be replaced with --comprise--

In Column 12, Line 64, Claim 9; "ligands" should be replaced with --ligand--

Signed and Sealed this
Twenty-ninth Day of November, 2011

David J. Kappos
*Director of the United States Patent and Trademark Office*